US00PP34321P2

(12) United States Plant Patent
Halladin

(10) Patent No.: US PP34,321 P2
(45) Date of Patent: Jun. 14, 2022

(54) ***PICEA PUNGENS* TREE NAMED 'INHWB'**

(50) Latin Name: *Picea pungens*
Varietal Denomination: INHWB

(71) Applicant: Early Morning LLC, Boring, OR (US)

(72) Inventor: Paul H. Halladin, Boring, OR (US)

(73) Assignee: Early Morning LLC, Boring, OR (US)

( * ) Notice: Subject to any disclaimer, the term of this patent is extended or adjusted under 35 U.S.C. 154(b) by 0 days.

(21) Appl. No.: 17/553,319

(22) Filed: Dec. 16, 2021

(51) Int. Cl.
*A01H 5/00* (2018.01)

(52) U.S. Cl.
USPC ..... Plt./213

(58) Field of Classification Search
USPC ..... Plt./213
See application file for complete search history.

*Primary Examiner* — Annette H Para

(74) *Attorney, Agent, or Firm* — Weatherly IP Solutions, LLC; Barbara Campbell

(57) ABSTRACT

A new and distinct variety of *Picea pungens* tree having a uniform, compact, and globose tree shape, is wider than tall, has blue-green leaves, and is tolerant to USDA Zones 2 to 8, is disclosed.

3 Drawing Sheets

Genus and species: *Picea pungens.*
Denomination: 'INHWB'.

BACKGROUND

'INHWB' is a new and distinct variety of *Picea pungens*. 'INHWB' originated from a branch mutation of the commercial line 'Hoopsii'(Unpatented) in February 2012 in Boring, Oreg.

'INHWB' was first asexually propagated in February 2012 in Boring, Oreg. via grafting onto *Picea abies* rootstock (Unpatented).

'INHWB' had been propagated for approximately 10 generations. 'INHWB' reproduces true to type in successive generations of asexual reproduction via grafting onto *Picea abies* rootstock (Unpatented).

SUMMARY

The following are the most outstanding and distinguishing characteristics of this new variety when grown under normal horticultural practices in Boring, Oreg.

1. Uniform, compact, and globose tree shape;
2. A wider than tall tree;
3. Blue-green leaves; and
4. Tolerant to USDA Zones 2 to 8.

DESCRIPTION OF THE PHOTOGRAPHS

This new *Picea pungens* tree is illustrated by the accompanying photographs which show the plant's overall plant habit including form and foliage. The photographs are of a 9-years and 10-month-old tree grown in a container in Boring, Oreg. taken in December 2021 under cloudy conditions. The colors shown are as true as can be reasonably obtained by conventional photographic procedures.

DETAILED DESCRIPTION

Figure 1:
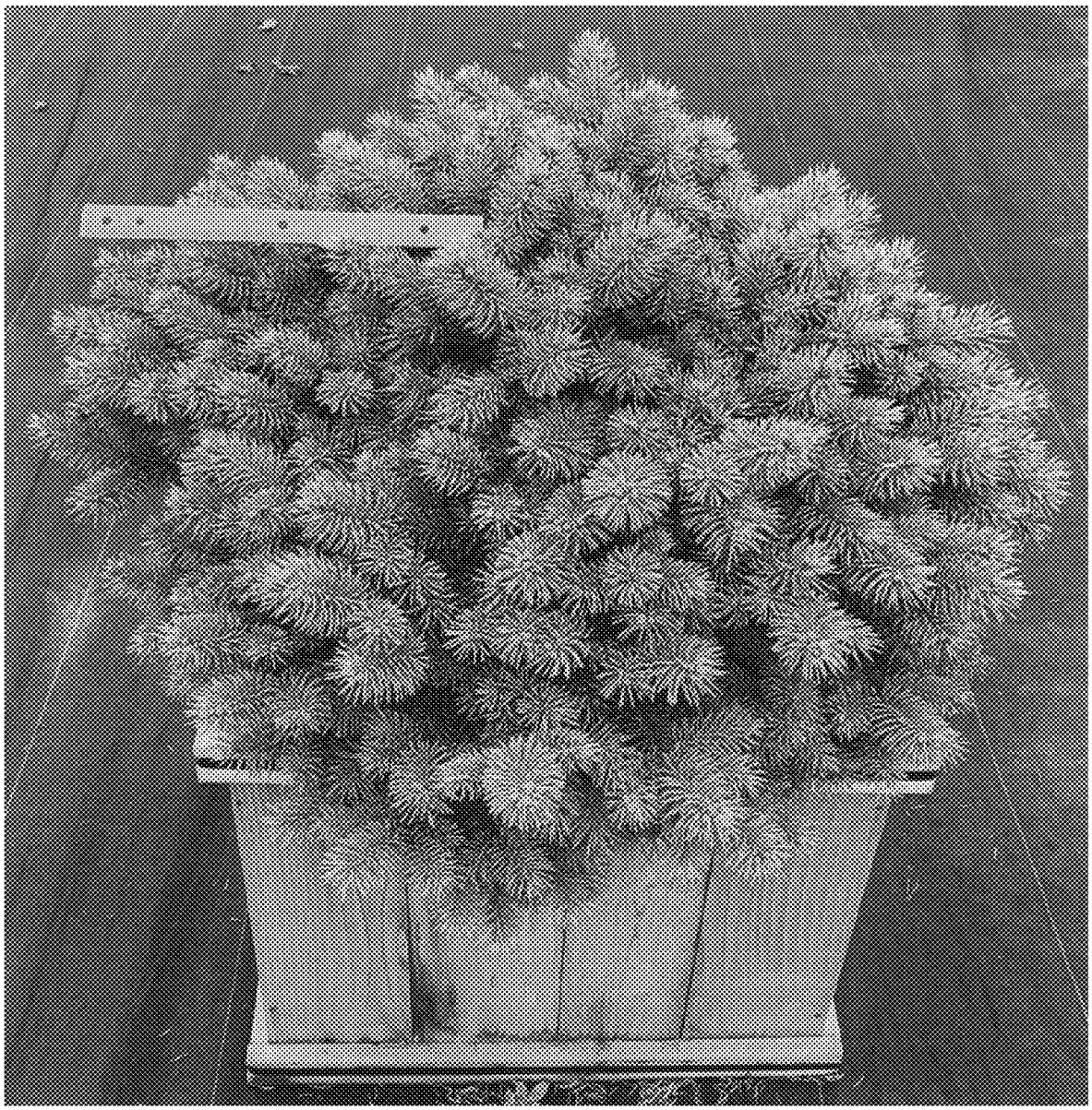
FIG. 1 shows the overall form of the whole tree of 'INHWB'.
Figure 2:
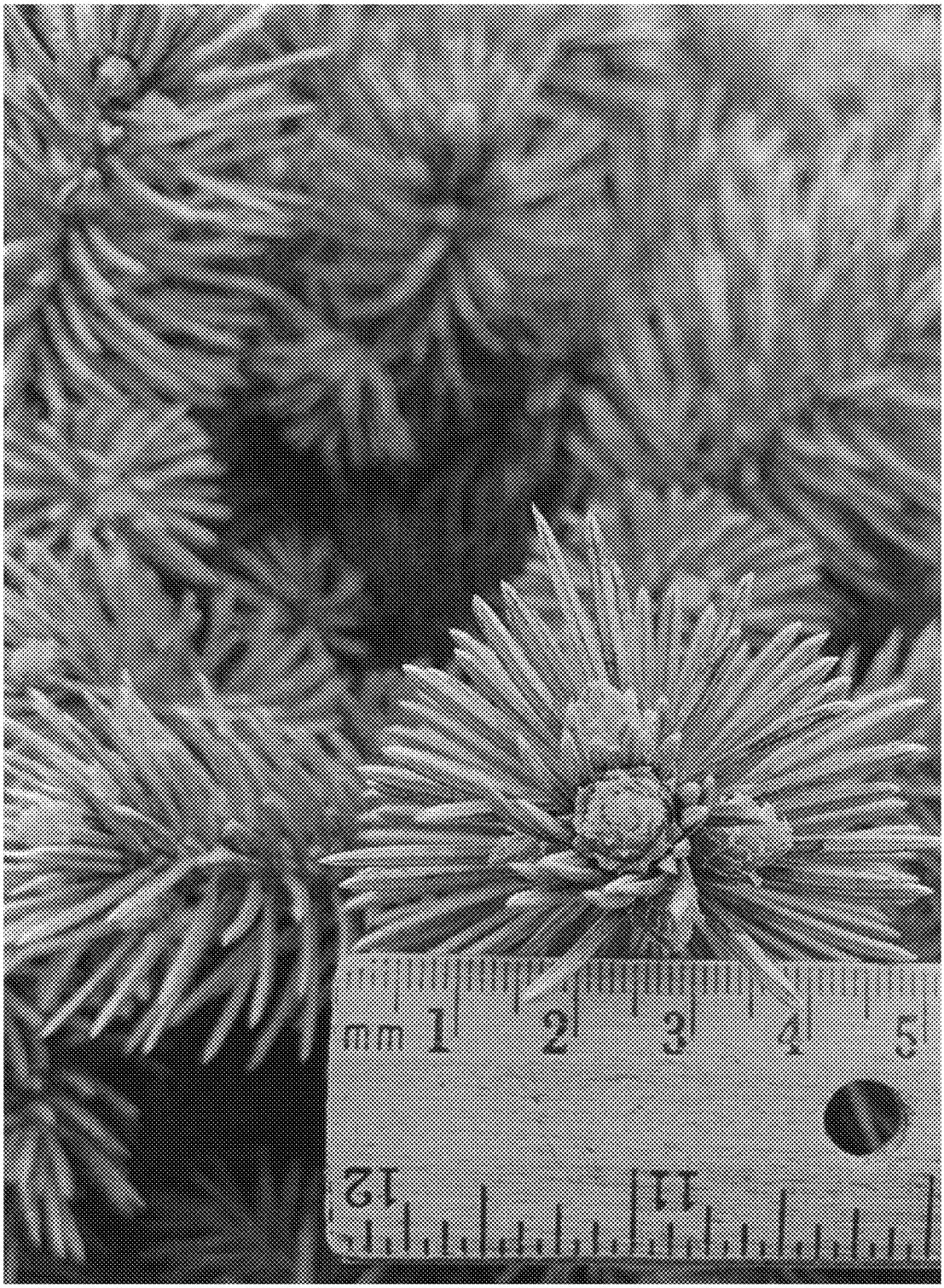
FIG. 2 shows a close-up of the buds and needles or leaves of the tree of FIG. 1.
Figure 3:
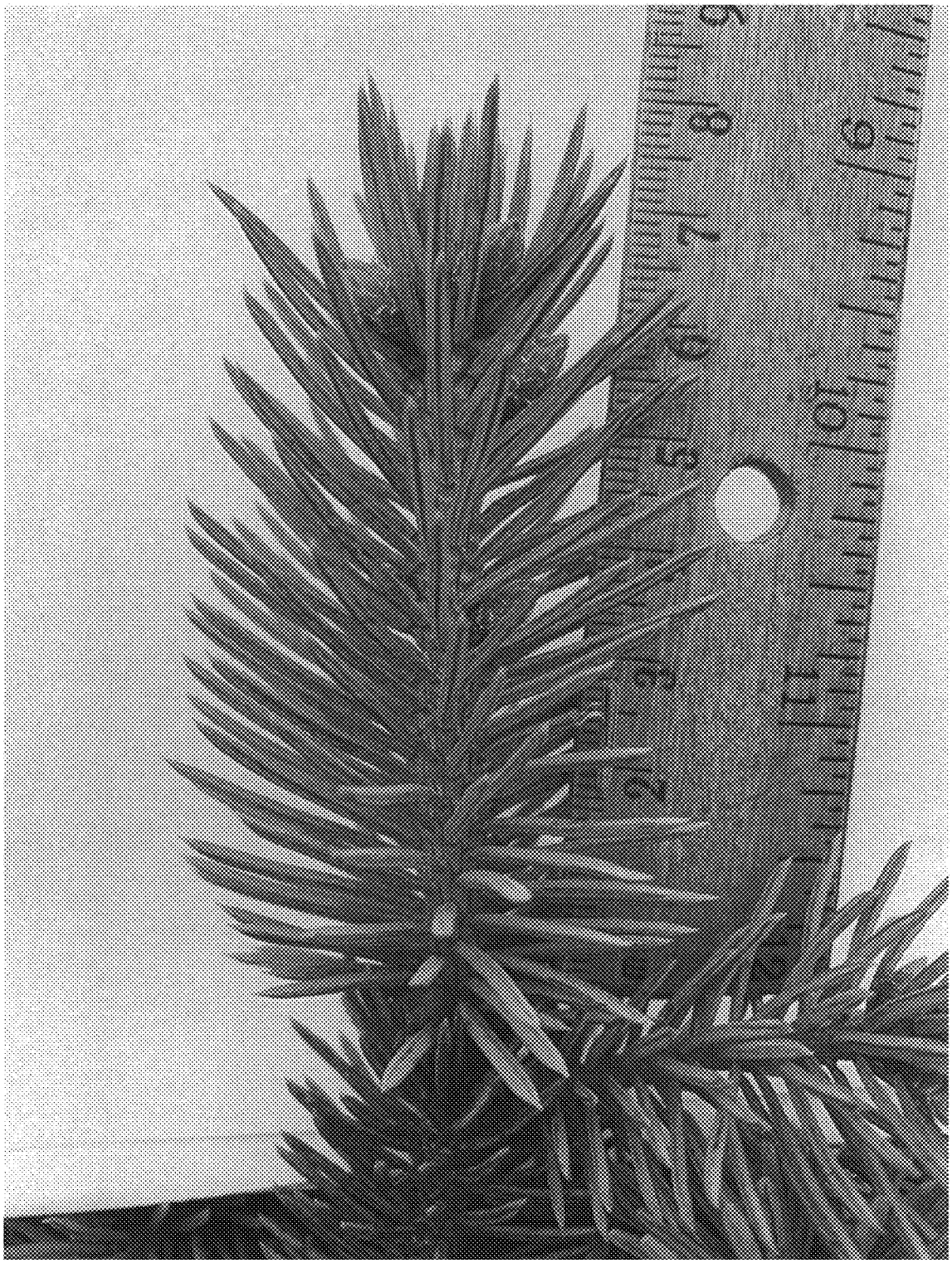
FIG. 3 shows a close-up of the terminal branch shoot of the tree of FIG. 1.

The following detailed descriptions set for the distinctive characteristics of 'INHWB'. The data which define these characteristics were collected outdoors in Boring, Oreg. in December 2021. The trees were 9-years and 10-month-old tree grown in a container in Boring, Oreg. when the descriptions were taken. Color references are to The R.H.S. Colour Chart of The Royal Horticultural Society of London (R.H.S.) 2001, except where general terms of ordinary dictionary significance are used.

Classification:

*Family.*—Pinaceae.
*Botanical.*—*Picea pungens.*
*Denomination.*—'INHWB'.

Tree:

*Type.*—Evergreen conifer.
*Shape.*—Uniform, compact, and globose; wider than tall.
*Growth and branching habit.*—Single flush, monopodial but lacking a dominant orthotropic shoot, branch shoots are plagiotropic of equivalent length.
*Propagation type.*—Grafting onto *Picea abies* rootstock (Unpatented).
*Height* (*from soil line*).—40 cm at 10 years.
*Width* (*horizontal plant diameter*).—80 cm at 10 years.
*Length of terminal* 1-*year shoots.*—4.0 cm to 8.0 cm.
*Length of subterminal* 1-*year shoots.*—3.5 cm to 5.5 cm.
*Diameter of trunk.*—6.5 cm at 10 years.
*Temperature tolerance or zones.*—USDA Zones 2 to 8.

Leaves (needles):

*Arrangement.*—Radial, single.
*Quantity of leaves per terminal one-year branch shoot.*—310 needles.
*Quantity of leaves per subterminal one-year branch shoot.*—85 needles.

*Shape.*—Needle-like, acicular.
*Apex.*—Acute.
*Base.*—Attenuate, attached to leaf peg.
*Margin.*—Entire, smooth.
*Leaf length, terminal shoot.*—Basal: 1.5 cm to 2.5 cm; Medial: 2.0 cm to 3.0 cm; Distal: 1.0 cm to 2.0 cm.
*Leaf length, subterminal shoot.*—Basal: 0.5 cm to 1.5 cm; Medial: 1.5 cm to 2.5 cm; Distal: 0.5 cm to 1.5 cm.
*Width.*—0.2 cm.
*Texture.*—Dull smooth covered with waxy layer.
*Pubescence.*—Absent.
*Mature leaf color for both upper and lower surfaces.*—RHS 112C (Blue-Green).
*Mature leaf color when wax rubbed off.*—RHS 189A (Greyed-Green).
*Petioles.*—Leaves are sessile on short peg.

Buds:
*Color.*—RHS 168C (Greyed-Orange).
*Bud shape.*—Broadly conical.
*Height.*—0.8 cm to 1.2 cm.
*Width.*—0.6 cm to 1.0 cm.

Cones: No male or female cones have been observed to date.

Disease/pest resistance: No specific disease or pest resistance has been observed to date.

COMPARISON WITH PARENTAL AND COMMERCIAL LINES

Table 1 shows a comparison of differences between 'INHWB' the mutation parent.

TABLE 1

Comparison with Mutation Parent

| Characteristic | 'INHWB' | Mutation Parent 'Hoopsii' |
|---|---|---|
| Shape | Globose | Broad upright |
| Growth rate per year | 4.0 cm to 8.0 cm | 22.0 cm to 38.0 cm |
| Size, height and width at 10-years-old | 40 cm × 80 cm | 230 cm × 135 cm |

Table 2 shows a comparison of the differences between 'INHWB' and the commercial *Picea pungens* tree 'Montgomery' (Unpatented).

TABLE 2

Comparison with Commercial Line

| Characteristic | 'INHWB' | 'Montgomery' |
|---|---|---|
| Immature shape | Uniform and globose | Irregular flattened mound |
| Mature shape | Globose - wider than tall | Pyramidal shape |
| Growth rate per year | 4.0 cm to 8.0 cm | 10.0 cm to 20.0 cm |
| Size height by width at 10 years | 40 cm × 80 cm | 90 cm × 105 cm |
| Color | RHS 112C (Blue-Green) | RHS 122B (Blue-Green) |

I claim:

1. A new and distinct variety of *Picea pungens* tree designated 'INHWB' as illustrated and described herein.

* * * * *